United States Patent [19]

Djordjević et al.

[11] 4,440,772

[45] Apr. 3, 1984

[54] ACID ADDITION SALTS OF DEXTROROTATORY ERGOT ALKALOIDS, A PROCESS FOR THE PREPARATION THEREOF AS WELL AS THEIR USE AS MEDICINES

[75] Inventors: Nebojša Djordjević; Rudolf Rućman; Sunčica Jovanović; Breda Bole-Vunduk; Tone Lavrič; Boža Lavrič; Cvetka Gruškovnjak; Ana Kocjan; Hermina Krmelj, all of Ljubljana, Yugoslavia

[73] Assignee: LEK, tovarna farmacevtskih in kemicnih izdelkov, n.sol.o., Yugoslavia

[21] Appl. No.: 269,212

[22] Filed: Jun. 2, 1981

Related U.S. Application Data

[62] Division of Ser. No. 58,332, Jul. 17, 1979, abandoned.

[30] Foreign Application Priority Data

Jul. 19, 1978 [YU] Yugoslavia ............................ 1736/78

[51] Int. Cl.³ .................... A61U 31/48; A61U 31/475
[52] U.S. Cl. ..................................... 424/261; 424/262
[58] Field of Search ............................... 424/261, 262

[56] References Cited

U.S. PATENT DOCUMENTS

| 1,435,187 | 11/1922 | Stoll | 544/346 |
| 2,447,214 | 8/1948 | Stoll et al. | 544/346 |
| 3,314,959 | 4/1967 | Hofmann et al. | 544/346 |
| 3,336,311 | 8/1967 | Hofmann et al. | 544/346 |
| 3,428,639 | 2/1969 | Stadler | 544/346 |
| 3,652,569 | 3/1972 | Stadler et al. | 544/346 |
| 3,755,328 | 8/1975 | Stadler et al. | 544/346 |
| 3,846,433 | 11/1974 | Stadler et al. | 544/346 |
| 4,145,549 | 3/1979 | Stadler | 544/346 |

FOREIGN PATENT DOCUMENTS 1158265 7/1969 United Kingdom ................ 544/346

OTHER PUBLICATIONS

Hofmann et al., Die Mutterkorn Alkaloide, (Stuttgart 1964), pp. 19-30.
Stoll, Helv. Chem. Acta., vol. 22, pp. 1283-1301 (1945).
Goodman et al, The Pharmacological Basis of Therapeutics, 5th Ed, 1975, pp. 872-880.
Stoll et al, Helv. Chem. Acta, vol. 26, pp. 1570-1601 (1943).

Primary Examiner—Stanley J. Friedman
Attorney, Agent, or Firm—Pollock, Vande Sande & Priddy

[57] ABSTRACT

Medicine containing salts of ergotaminine, ergosinine, ergocryptinine, ergocristinine, and ergocorninine and use for treating arterial hypertension, heart insufficiency, heart arrhythmia or cephalalgia.

28 Claims, No Drawings

ACID ADDITION SALTS OF DEXTROROTATORY ERGOT ALKALOIDS, A PROCESS FOR THE PREPARATION THEREOF AS WELL AS THEIR USE AS MEDICINES

This is a division of application Ser. No. 58,332, filed July 17, 1979, now abandoned.

The present invention relates to acid addition salts of dextrorotatory ergot alkaloids, a process for the preparation thereof as well as their use as medicines.

More particularly, the present invention relates to acid addition salts of ergotaminine, ergosinine, ergocryptinine, ergocristinine and ergocorninine of the general formula

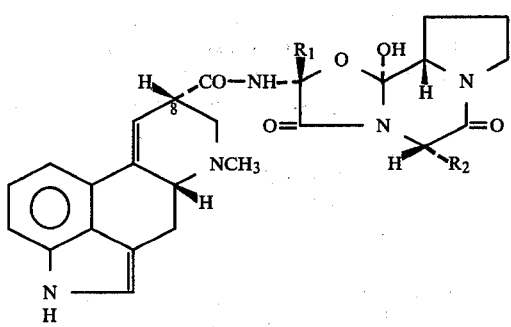

wherein the meanings for $R_1$ and $R_2$ are

| | $R_1$ | $R_2$ |
|---|---|---|
| in ergotaminine | $-CH_3$ | $-CH_2C_6H_5$ |
| in ergosinine | $-CH_3$ | $-CH_2CH{\scriptstyle\begin{array}{l}CH_3\\CH_3\end{array}}$ |
| in ergocryptinine | $-CH{\scriptstyle\begin{array}{l}CH_3\\CH_3\end{array}}$ | $-CH_2CH{\scriptstyle\begin{array}{l}CH_3\\CH_3\end{array}}$ |
| in ergocristinine | $-CH{\scriptstyle\begin{array}{l}CH_3\\CH_3\end{array}}$ | $-CH_2C_6H_5$ |
| in ergocorninine | $-CH{\scriptstyle\begin{array}{l}CH_3\\CH_3\end{array}}$ | $-CH{\scriptstyle\begin{array}{l}CH_3\\CH_3\end{array}}$ | which salts are suitable for the treatment of arterial hypertension, heart insufficiency, heart arrhythmia and cephalalgia.

Ergotaminine, ergosinine, ergocryptinine, ergocristinine and ergocorninine differ from native levorotatory ergot alkaloids in the configuration at 8-position. They result from the epimerisation of native alkaloids (A. Hofmann, Die Mutterkornalkaloide, F. Enke Verlag, Stuttgart 1964, pp. 20-30). They are 5R,8S-lysergic acid derivatives and D-isolysergic acid derivative, respectively.

So far they have been considered as not pharmacologically active and as such not useful in therapy, whereby they differed from levorotatory isomers ergotamine, ergosine, ergocryptine, ergocristine and ergocornine, which are lysergic acid derivatives.

Consequently, in patent literature as well as in other literature several processes for isolation of levorotatory isomers, which are largely used in medicine, are described, whereas processes for isolation of dextrorotatory isomers, which have not been in use till now, are not present in said literature. Hitherto only processes for mutual conversion of the two isomeric forms by means of heating in methanol or formation of insoluble salts have been disclosed, which processes can only be used for scientific purposes (A. Stoll, A. Hofmann. Helv. chim. acta 26, 1943, p. 1570; A. Stoll, Helv. chim. acta 28, 1945, p. 1283; A. Hofmann, Die Mutterkornalkaloide, F. Enke Verlag, Stuttgart 1964). Fresh ergots contain only a small amount of dextrorotatory isomers. Greater quantities of said isomers can be found in the drug stored for some time. As both isomeric forms are reversible and easily pass from one form into another, the dextrorotatory isomers are formed during the production process in spite of various precautions taken in order to inhibit said passing. The greatest concentration of ergotaminine, ergosinine, ergocryptinine, ergocristinine and ergocorninine is achieved in crystallization liquors left after the crystallization of levorotatory isomers and amounts to 50-80%. Beside alkaloids said liquors also contain considerable amounts of coloured ballast materials and decomposition products.

In our Yugoslavian patent application P 1465/78 a process for isolation of pure ergotaminine, ergosinine, ergocryptinine, ergocristinine and ergocorninine from the crystallization liquors left after the crystallization of levorotatory isomers is disclosed, which is characterized in that dried crystallization liquors are dissolved in an about 10-fold amount of methylene chloride and cromatographed in the ratio 1:100 over neutral aluminum oxide (activity III to IV according to Brockmann) by means of a 100:0.2-1.4 (vol./vol.) mixture of methylene chloride and n-propanol.

Thus the production of the dextrorotatory isomers on industrial scale as well as their use in therapy becomes possible.

Since dextrorotatory ergot alkaloids are weakly water-soluble and as such not suitable for therapeutic use, they are converted into their physiologically compatible acid addition salts. The biological activity of dextrorotatory ergot alkaloids can be characterized as distinctly surprising, as it has been the general opinion up to now that said ergot alkaloids are biologically inactive (L. Goodman and A. Gilman, The Pharmaceutical Basis of Therapeutics, 5th ed., New York 1975; P. A. Stadler and P. Stütz, The Alkaloids, Vol. XV, The Ergot Alkaloids, Chemistry and Physiology 1975, Academic Press, New York, p. 30 ff.) and do not form stable salts with acids at all (The Merck Index, 9th ed., Merck & Co., Inc., 1976, pp. 476, and 479; A. Hofmann, Die Mutterkornalkaloide, F. Enke Verlag, Stuttgart 1964, pp. 21-28).

It has now been found that acid addition salts of dextrorotatory ergot alkaloids ergotaminine, ergosinine, ergocryptinine, ergocristinine and ergocorninine are prepared by dissolving said dextrorotatory ergot alkaloids in a solvent, which is inert against reaction partners and which contains 1 to 1.7 moles of required inorganic or organic acid per mole of said dextrorotatory ergot alkaloid, and by precipitating the acid addition salt with addition of a precipitation solvent.

As the solvent which is inert against the reaction partners, preferably alkanol with 1 to 3 carbon atoms or ketone with 3 to 6 carbon atoms is used.

As the precipitation solvent preferably an aliphatic ether with 4 to 8 carbon atoms is used.

As the acid a strong inorganic or a strong organic acid with physiologically compatible anion can be employed. As inorganic acids e.g. hydrochloric acid, hydrobromic acid, nitric acid are suitable, as organic acids methanesulfonic acid, ethanesulfonic acid and haloacetic acids, such as trichloroacetic acid, trifluoroacetic acid etc. can be used. As previously mentioned, the acid addition salts of said dextrorotatory ergot alkaloids exhibit interesting pharmacological properties as follows.

1. ACUTE TOXICITY

The mean lethal dose $LD_{50}$ was determined in male mice weighing 18 to 25 g at intraperitoneal administration. The volume of injected solution was 0.01 ml/g of body weight. In the following Table I acute toxicity of dextrorotatory ergot alkaloids in comparison with levorotatory ergot alkaloids 24 hours after the intraperitoneal administration is given.

TABLE I

| Substance | $LD_{50}$ (mg/kg of body weight) |
| --- | --- |
| ergotaminine methanesulfonate | >300 |
| ergosinine methanesulfonate | 244.7++ |
| ergocryptinine methanesulfonate | >520 |
| ergocristinine methanesulfonate | >600 |
| ergocorninine methanesulfonate | >520 |
| ergotamine tartrate | 412.0 (322.4 to 526.5)+ |
| ergosine methanesulfonate | 206.3 (158.2 to 268.9)+ |
| ergocryptine methanesulfonate | 187.9++ |
| ergocristine methanesulfonate | 234.0 (123.0 to 44.6)+ |

+calculated by method of J. Litchfield and F. Wilcoxon, J. Pharmacol. exp. Therap. 96 (1949), 99.
++calculated by method of G. Korber, Arch. exp. path.Pharmakol. 162 (1931), 480.

It is evident from the above results that dextrorotatory ergot alkaloids are less toxic than levorotatory ergot alkaloids.

2. THE EFFECT ON ARTERIAL PRESSURE

(a) The effect on blood pressure and heart pulsation in normotensive narcotized rats The artery Carotis communis was cannulated in narcotized rats (variety Wistar) and the blood pressure was recorded on a dynograph (type Beckmann) over a minitransducer. The frequency of heart pulsation was recorded by a cardiotachometer on the same dynograph. Dextrorotatory ergot alkaloids were administered in the form of methanesulfonate salt into Vena jugularis by means of an apparatus for slow infusion (B. Melsungen) in doses of 0.15, 0.45 and 1.5 mg/kg of body weight.

The results of experiments showed that dextrorotatory ergot alkaloids did not affect blood pressure and frequency of heart pulsation.

(b) The effect on blood pressure drop in rats with cut spinal cord

Rats (variety Wistar) in urethane narcosis were cut their spinal cord in the region of the second cervical vertebra and connected to an artificial breathing apparatus (B. Melsungen). By this intervention the central regulation of blood pressure was eliminated. In so treated animals blood pressure dropped for about 50 mm Hg. The experiment was supposed to show whether the examined substances directly affected the smooth muscles of blood vessels.

The results of the experiments showed that the acid addition salts of ergotaminine, ergocryptinine and ergocorninine in a dose of 1.5 mg/kg of body weight caused a long-duration hypertension lasting more than 60 minutes.

The same effect was induced by ergosinine only in a dose of 4.5 mg/kg of body weight, whereas ergocristinine showed no effect even in a dose of 4.5 mg/kg of body weight.

The frequency of heart pulsation was reduced during the experiment with any of said dextrorotatory ergot alkaloids except with ergocristinine.

It is evident from the above results that ergotaminine, ergocryptinine, ergosinine and ergocorninine, similar as dihydroergotoxine and dihydroergotamine, show vasoconstrictory effect, i.e. they cause the contraction of smooth muscles of blood vessels (E. Rothlin and A. Cerletti, Verh. dtsch. Ges. Kreislaufforsch. 15, 1949, 158).

(c) The effect on arterial pressure of spontaneously hypertensive rats

For the experiment groups of 10 spontaneously hypertensive rats (variety Okamoto Aoki $F_{32}$) of both sexes, weighing from 200 to 250 g, were used. The acid addition salts of said dextrorotatory ergot alkaloids were administered intraperitoneally in doses of 50 mcg/kg of body weight and systolic blood pressure was measured on the rats' tails by means of plethysmographic method (K. Okamoto and K. Aoki, Jap. Circulat. J. 27, 1963, 282).

The results of experiments are cited in the following Table II.

TABLE II

| | Systolic blood pressure in mm Hg | | | | | |
| --- | --- | --- | --- | --- | --- | --- |
| | | day | | | | |
| Substance | control | 2 | 4 | 6 | 8 | 10 |
| ergotaminine methanesulfonate | 189 | 162 | 143 | 131 | 144 | 150 |
| ergosinine methanesulfonate | 180 | 169 | 152 | 140 | 141 | 138 |
| ergocryptinine methanesulfonate | 189 | 181 | 176 | 168 | 161 | 160 |
| ergocristinine methanesulfonate | 187 | 183 | 177 | 169 | 160 | 152 |
| ergocorninine methanesulfonate | 190 | 182 | 176 | 166 | 160 | 161 |
| ergotamine tartrate | 179 | 174 | 170 | 172 | 173 | 172 |
| ergosine methanesulfonate | 188 | 183 | 178 | 176 | 175 | 177 |

The results of experiments show that all mentioned dextrorotatory alkaloids gradually induce systolic blood pressure drop in spontaneously hypertensive rats. The strongest effect is exhibited by ergosinine and ergotaminine.

Most levorotatory ergot alkaloids do not affect the systolic blood pressure of spontaneously hypertensive rats.

2. THE EFFECT ON HEART

In experiments in normotensive narcotized rats with cut spinal cord, the dextrorotatory ergot alkaloids in active doses induce slower heart action, i.e. bradycardia. This effect is established for all known ergot alkaloids and the derivatives thereof, e.g. ergotoxine, ergotamine, dihydroergotoxine, dihydroergotamine and others (E. Rothlin, Wien. Klin. Wschr. 62, 1950, 893).

The effect of dextrorotatory ergot alkaloids according to the invention on heart in vitro was examined on isolated heart of a guinea pig by the modified Langendorff's method (Zalar et al., Poll. Chim. Farmac. 114, 1975, 146). Alkaloids were infused by an apparatus for slow infusion (B. Melsungen).

The results of the experiments are shown in the following Table III.

TABLE III

| Substance | Dose (mcg/g of heart) | (+)inotropic (maximum) in % | (−)chronotropic (maximum) in % |
|---|---|---|---|
| ergotaminine methanesulfonate | 5.59 | 32 | 20 |
| ergosinine methanesulfonate | 0.65 | 103 | 23 |
| ergocryptinine methanesulfonate | 0.04 | 111 | 21 |
| ergocristinine methanesulfonate | 4.98 | 9 | 12 |
| ergocorninine methanesulfonate | 4.90 | — | 11 |
| ergotamine tartrate | 0.65 | 75 | 30 |
| ergosine methanesulfonate | 0.57 | 49 | 17 |

From the given results it is evident that ergotaminine, ergosinine and ergocryptinine exhibit an effect on isolated heart, which is qualitatively similar to that of ergotamine, ergosine and dihydroergotamine.

Ergosinine and especially ergocryptinine have a quantitatively greater effect on the strength of heart contraction.

The effect of ergotaminine, ergosinine and ergocrystinine on heart in situ was examined in rats. The thorax of narcotized rats (0.7 ml of 25% urethane solution per 100 g of the body weight, administered subcutaneously) was opened. The heart was placed into a special basket with a balloon, which was connected over a polyethylene cannula to a transducer "Mini Pressure Transducer—Beckmann" and dynograph Beckmann. As the left wall of the ventricle leant against the balloon, the contraction of the ventricle could be recorded. Over a tracheal tube the rats were connected to an artificial breathing apparatus.

The results showed that ergotaminine, ergosinine and ergocristinine in doses of 250 and 300 mcg/kg intravenously (with the apparatus for slow infusion B. Melsungen) increased the strength of heart contraction for 15% and 30%, resp.

4. THE EFFECT ON ARRHYTHMIA INDUCED BY ADRENALIN

It is well known that levorotatory ergot alkaloids and derivatives thereof totally or partly inhibit the occurrence of heart arrhythmias induced by adrenalin.

For experiments, guinea pigs of both sexes, weighing from 400 to 550 g, were used. The narcotized animals (urethane 1.6 g/kg of body weight, intraperitoneally) were at first intravenously administered adrenalin (0.02 mg/kg) and then dextrorotatory ergot alkaloids. 1 hour and 1.5 hours after the administration of dextrorotatory ergot alkaloids, adrenalin was again administered intravenously (0.02 mg/kg) and the presence as well as duration of arrhythmias was ascertained.

The results of experiments are shown in the following Table IV.

TABLE IV

| Substance | Dose (mg/kg intraperitoneally) | Shortening of arrhythmia duration in % of control |
|---|---|---|
| ergotaminine methanesulfonate | 2.0 | 28 |
| ergosinine methanesulfonate | 2.0 | 79 |
| ergocryptinine methanesulfonate | 2.0 | 63 |
| ergocristinine methanesulfonate | 2.0 | 32 |
| ergocorninine methanesulfonate | 2.0 | 46 |
| ergotamine tartrate | 2.0 | 63 |
| ergosine methanesulfonate | 2.0 | 84 |

It is evident from the shown results that the duration of arrhythmia is most efficiently shortened by ergosinine, followed by ergocryptinine, ergocorninine, ergocristinine and ergotaminine. Levorotatory ergot alkaloids exhibit a somewhat stronger effect against arrhythmia and adrenalin.

5. THE EFFECT ON THE FUNCTION OF THE PUPIL

The phenomenon of mydriasis induced by ergot alkaloids results from the stimulation of alpha-adrenergic receivers of the dilatating pupil muscle (Z. Votava et al., Arch. int. Pharmacodin. 45, 1958, 114).

The mydriatic effect of dextrorotatory ergot alkaloids administered intravenously was determined with a monocular measuring magnifying glass by Polewka's method (A. R. Turner, Screening Methods in Pharmacology, 1965, p. 174 ff.).

The size of the pupil was measured at first before the administration of the substance and then 15, 30 and 60 minutes after intravenous administration of alkaloids into the mouse tail (dose 5 mg/kg of body weight).

The results of experiments are shown in the following Table V.

TABLE V

| Substance | The increase of pupil widening in comparison with the control in % | | |
|---|---|---|---|
| | after 15 min. | after 30 min. | after 60 min. |
| ergotaminine methanesulfonate | 66.3 | 69.8 | 30.3 |
| ergosinine methanesulfonate | 135.0 | 122.5 | 32.5 |
| ergocryptinine methanesulfonate | 117.4 | 91.6 | 32.2 |
| ergocristinine methanesulfonate | 48.7 | 10.3 | 2.5 |
| ergocorninine methanesulfonate | 52.7 | 36.1 | 19.4 |
| ergotamine tartrate | 73.3 | 22.8 | 4.6 |
| ergosine methanesulfonate | 115.6 | 110.5 | 39.7 |

It is evident from the shown results that dextrorotatory ergot alkaloids induce a mydriatic effect similar to the effect of levorotatory ergot alkaloids. The strongest mydriatic effect was exhibited by ergosinine and ergocryptinine.

On the basis of pharmacological properties it can be established that the dextrorotatory ergot alkaloids according to the invention have a hypotensive effect, as shown by experiments on spontaneously hypertensive rats, affect the contraction strength of the heart ventricle and the frequency of heart pulsation, as shown by experiments on the isolated heart of guinea pig and on the heart of rat in situ, are effective against arrhythmias, as shown by experiments on guinea pigs at arrhythmias induced by adrenalin, have a spasmogenic effect, as shown by experiments on spinal rats, and an agonistic effect on alpha-receivers, as shown by experiments on the mouse pupil.

On the basis of said properties, the dextrorotatory ergot alkaloids ergotaminine, ergosinine, ergocryptinine, ergocristinine and ergocorninine can be used in the treatment of arterial hypertension, heart insufficiency, heart arrhythmia and cephalalgia.

Said dextrorotatory alkaloids in the form of their physiologically compatible acid addition salts are used as medicines for enteral and parenteral administration. The pharmaceutical compositions are formulated by adding usual inorganic and organic adjuvants. For tablets and dragees there are added e.g. lactose, starch, talc, magnesium stearate etc. For solutions and suspensions there are added e.g. water, alcohols, glycerine, vegetable oils etc. For suppositories there are added e.g. vegetable oils, hardened oils and waxes. The formulations can also contain suitable preservatives, stabilizers, surfactants, dissolving imtermediaries, sweetening agents and dye stuffs.

A suitable daily dose for dextrorotatory ergot alkaloids according to the invention in the form of their physiologically compatible acid addition salts amounts to 0.01–1.0 mg/kg of body weight.

The invention is illustrated by the following Examples.

EXAMPLE 1

Ergocristinine methanesulfonate

Ergocristinine (1.25 g; 0.05 mmoles) was dissolved in absolute ethanol (25 ml), containing methanesulfonic acid (0.15 ml; 2.31 mmoles). After clarifying, the solution was slowly poured into absolute diethylether (350 ml) while stirring. The precipitated salt was filtered off and dried in vacuo. Ergocristinine methanesulfonate (1.40 g; 96.4% of the theory) with a melting point of 170°–180° C. was obtained.

EXAMPLE 2

Ergocorninine methanesulfonate

Ergocorninine (1.50 g; 2.67 mmoles) was dissolved in absolute ethanol (20 ml), containing methanesulfonic acid (0.21 ml; 2.93 mmoles). The clear solution was poured into absolute diethylether (300 ml) while stirring. The precipitated salt was filtered off and dried in vacuo. Ergocorninine methanesulfonate (1.64 g; 98.2% of the theory) with a melting point of 178°–179° C. was obtained.

EXAMPLE 3

Ergocryptinine methanesulfonate

Ergocryptinine (2.30 g; 4 mmoles) was dissolved in absolute ethanol (20 ml), containing methanesulfonic acid (0.3 ml; 4.62 mmoles). The clear solution was poured into absolute diethylether (300 ml) while stirring. The precipitated salt was filtered off and dried in vacuo. Ergocryptinine methanesulfonate (2.5 g; 97.6% of the theory) with a melting point of 174°–175° C. was obtained.

EXAMPLE 4

Ergosinine methanesulfonate

Ergosinine (5.48 g; 10 mmoles) was dissolved in absolute ethanol (60 ml), containing methanesulfonic acid (0.72 ml; 11 mmoles). The clear solution was poured into absolute diethylether (600 ml). The precipitated salt was filtered off and dried in vacuo. Ergosinine methanesulfonate (6.05 g; 98.7% of the theory) with a melting point of 190°–192° C. was obtained.

EXAMPLE 5

Ergotaminine methanesulfonate

Ergotaminine (1.25 g; 2.15 mmoles) was dissolved in absolute ethanol (53 ml), containing methanesulfonic acid (0.16 ml; 2.46 mmoles). The clear solution was poured into absolute diethylether (430 ml). The precipitated salt was filtered off and dried in vacuo. Ergotaminine methanesulfonate (1.3 g; 99.2% of the theory) with a melting point of 184°–187° C. was obtained.

EXAMPLE 6

Ergotaminine ethanesulfonate

Ergotaminine (0.58 g; 1 mmole) was converted, as in Example 5, to an addition salt with ethanesulfonic acid (0.12 g; 1.1 mmoles). Ergotaminine ethanesulfonate (0.63 g; 91.3% of the theory) with a melting point of 171°–173° C. was obtained.

EXAMPLE 7

Ergotaminine hydrochloride

Ergotaminine (0.58 g; 1 mmole) was converted, as in Example 5, to an addition salt with concentrated hydrochloric acid (0.16 ml; 1.6 mmoles). Ergotaminine hydrochloride (0.59 g; 95.1% of the theory) with a melting point of 205° C. (dec.) was obtained.

EXAMPLE 8

Ergotaminine trifluoroacetate

Ergotaminine (0.58 g; 1 mmoles) was converted, as in Example 5, to an addition salt with trifluoroacetic acid (0.13 g; 1.14 mmoles). Ergotaminine trifluoroacetate (0.47 g; 67.7% of the theory) with a melting point of 178°–180° C. was obtained.

EXAMPLE 9

Ergotaminine trichloroacetate

Ergotaminine (0.58 g; 1 mmole) was converted, as in Example 5, to an addition salt with trichloroacetic acid (0.18 g; 1.1 mmoles). Ergotaminine trichloroacetate (0.21 g; 28.3% of the theory) with a melting point of 238° C. (dec.) was obtained.

EXAMPLE 10

| Tablets | |
| --- | --- |
| Composition | mg/tablet |
| the active substance according to the invention | 30 |
| lactose | 218 |
| starch | 27 |
| talc | 13 |
| tragacanth | 10 |

-continued

| Tablets | |
|---|---|
| Composition | mg/tablet |
| magnesium stearate | 2 |
| total | 300 mg |

EXAMPLE 11

| Capsules | |
|---|---|
| Composition | mg/capsule |
| the active substance according to the invention | 20 |
| lactose | 280 |
| total | 300 mg |

EXAMPLE 12

| Injection solution | |
|---|---|
| Composition | weight in mg |
| Active substance according to the invention | 1.00 |
| sodium carboxymethylcellulose | 1.50 |
| polyvinyl pyrrolidone | 5.50 |
| lecithin | 3.20 |
| benzyl alcohol | 0.01 |
| buffer | q.s. |
| bidistilled water | ad 1 ml |
| total | 1 ml |

What is claimed is:

1. A process for the treatment of a condition selected from the group of arterial hypertension, heart insufficiency, heart arrhythmia or cephalalgia, or for inducing a vasoconstrictory effect, which comprises administering to a host in need of said treatment a physiologically active amount of a physiologically compatible acid addition salt of ergotaminine, ergosinine, ergocryptinine, ergocristinine or ergocorninine.

2. The process of claim 1 which is for the treatment of arterial hypertension.

3. The process of claim 1 which is for the treatment of heart insufficiency.

4. The process of claim 1 which is for the treatment of hear arrhythmia.

5. The process of claim 1 which is for the treatment of cephalagia.

6. The process of claim 1 wherein the daily dose of said addition salt is 0.01–1.0 mg/kg of body weight.

7. The process of claim 1 wherein the salt is administered in the form of a tablet or dragee.

8. The process of claim 7 wherein said tablet of dragee contains at least one of lactose, starch, talc, or magnesium stearate.

9. The process of claim 1 wherein said salt is administered as a solution or suspension.

10. The process of claim 9 wherein said solution or suspension contains at least one of water, an alcohol, glycerine, or a vegetable oil.

11. The process of claim 1 wherein said salt is administered in the form of a suppository.

12. The process of claim 11 wherein said suppository contains at least one of a vegetable oil, hardened oil, or wax.

13. The process of claim 1 wherein said addition salt is a salt of ergotaminine.

14. The process of claim 1 wherein said addition salt is a salt of ergosinine.

15. The process of claim 1 wherein said addition salt is a salt of ergocryptinine.

16. The process of claim 1 wherein said addition salt is a salt of ergocristinine.

17. The process of claim 1 wherein said addition salt is a salt of ergocorninine.

18. The process of any one of claims 1, 13, 14, 15, 16 or 17 wherein said acid is selected from the group of hydrochloric acid, hydrobromic acid, nitric acid, methanesulfonic acid, ethane sulfonic acid, trichloroacetic acid or trifluoroacetic acid.

19. The process of claim 14 which is for the treatment of cephalalgia or for inducing a vasoconstricting effect.

20. The process of claim 14 which is for the treatment of cephalalgia.

21. The process of claim 14 which is for inducing a vasoconstricting effect.

22. The process of claim 14 wherein the salt is a salt of ergosinine with an organic acid.

23. The process of claim 14 wherein the salt is a salt of ergosinine with a strong organic acid.

24. The process of claim 14 wherein the salt is a salt of ergosinine with methanesulfonic, ethanesulfonic, or a haloacetic acid.

25. The process of claim 14 wherein the salt is ergosinine methane sulfonate.

26. The process of claim 14 wherein the daily dose of said acid addition salt is 0.01 to 1.0 mg/kg of body weight.

27. The process of claim 14 wherein the salt is administered in the form of a tablet or dragee.

28. The process of claim 14 wherein the salt is administered as a solution or suspension.

* * * * *